(12) United States Patent
Goto et al.

(10) Patent No.: US 7,446,192 B2
(45) Date of Patent: Nov. 4, 2008

(54) GENE PARTICIPATING IN ACETIC ACID TOLERANCE, ACETIC ACID BACTERIA BRED USING THE GENE, AND PROCESS FOR PRODUCING VINEGAR WITH THE USE OF THE ACETIC ACID BACTERIA

(75) Inventors: Hidetsugu Goto, Handa (JP); Shigeru Nakano, Chita-gun (JP)

(73) Assignee: Mitsukan Group Corporation, Handa-shi (JP)

( * ) Notice: Subject to any disclaimer, the term of this patent is extended or adjusted under 35 U.S.C. 154(b) by 557 days.

(21) Appl. No.: 10/507,446

(22) PCT Filed: Mar. 12, 2003

(86) PCT No.: PCT/JP03/02946

§ 371 (c)(1), (2), (4) Date: Sep. 13, 2004

(87) PCT Pub. No.: WO03/078635

PCT Pub. Date: Sep. 25, 2003

(65) Prior Publication Data

US 2006/0154351 A1 Jul. 13, 2006

(30) Foreign Application Priority Data

Mar. 15, 2002 (JP) ............................. 2002-072931

(51) Int. Cl.
  *C07H 21/04* (2006.01)
(52) U.S. Cl. .................................... 536/23.7; 536/23.2
(58) Field of Classification Search ........................ None
  See application file for complete search history.

(56) References Cited

U.S. PATENT DOCUMENTS

| 4,654,306 A | 3/1987 | Entani et al. ................. 435/253 |
| 5,914,257 A | 6/1999 | Fukaya et al. ................ 435/190 |

FOREIGN PATENT DOCUMENTS

| JP | 60-009489 | 1/1985 |
| JP | 60-180581 | 9/1985 |
| JP | 02-002364 | 1/1990 |
| JP | 03-219878 | 9/1991 |

OTHER PUBLICATIONS

Ikushiro et al., J. Biol. Chem., 276:18249-18256, 2001.*
Bowie et al (Science, 1990, 247:1306-1310).*
Burgess et al (J. of Cell Bio. 111:2129-2138, 1990).*
Lazar et al. (Molecular and Cellular Biology, 1988, 8:1247-1252).*
Bork (Genome Research, 2000, 10:398-400).*
Stratagene catalog (Stratagene Cloning Systems, 1993, p. 88).*
Invitrogen catalog (Invitrogen, 2001, p. 35).*
Goto et al., "Comparative Analysis of Phospholipids for Two *Acetobacters* Producing Acetic Acid at High and Moderate Concentrations," Nakanochuken Nippon Yuka Gakkaishi (Journal of Japan Oil Chemists' Society), vol. 49, No. 4, 2000, pp. 35-41.
Jenkins et al., "Role for de Novo Sphingoid Base Biosynthesis in the Heat-induced Transient Cell Cycle Arrest of *Saccharomyces cerevisiae*," Journal of Biological Chemistry, vol. 276, No. 11, Mar. 16, 2001, pp. 8574-8581.
Ikushiro et al., "A Water-soluble Homodimeric Serine Palmitoyltransferase from *Sphingomonas paucimobilis* EY2395T Strain," Journal of Biological Chemistry, vol. 276, No. 21, May 25, 2001, pp. 18249-18256.
Steiner et al., "Proteins Induced during Adaptation of *Acetobacter aceti* to High Acetate Concentrations," Applied and Environmental Microbiology, vol. 67, No. 12, Dec. 2001, pp. 5474-5481.

* cited by examiner

*Primary Examiner*—Robert B Mondesi
*Assistant Examiner*—Brian J Gangle
(74) *Attorney, Agent, or Firm*—Morgan & Finnegan, LLP

(57) ABSTRACT

The present invention is intended to provide novel genes participating in acetic acid tolerance of acetic acid bacteria, and a method of improving acetic acid tolerance of microorganisms, particularly that of acetic acid bacteria by using the genes, further a method of efficiently producing vinegar with acetic acid at higher concentration by using acetic acid bacteria whose acetic acid tolerance is improved. In the present invention, novel genes having a function for improving acetic acid tolerance on practical level were cloned from practical acetic acid bacteria belonging to the genus *Gluconacetobacter* by a method of obtaining genes from chromosomal DNA library that enable to grow on the medium at a high concentration of acetic acid. Further, in transformants in which the genes were introduced into acetic acid bacteria, acetic acid tolerance was remarkably increased, and when the transformants are subjected to aeration culture in the presence of ethanol, the growth lag-time can be shortened, and the growth rate can also be improved, moreover the final acetic acid concentration can be remarkably improved.

2 Claims, 6 Drawing Sheets

Figure 4
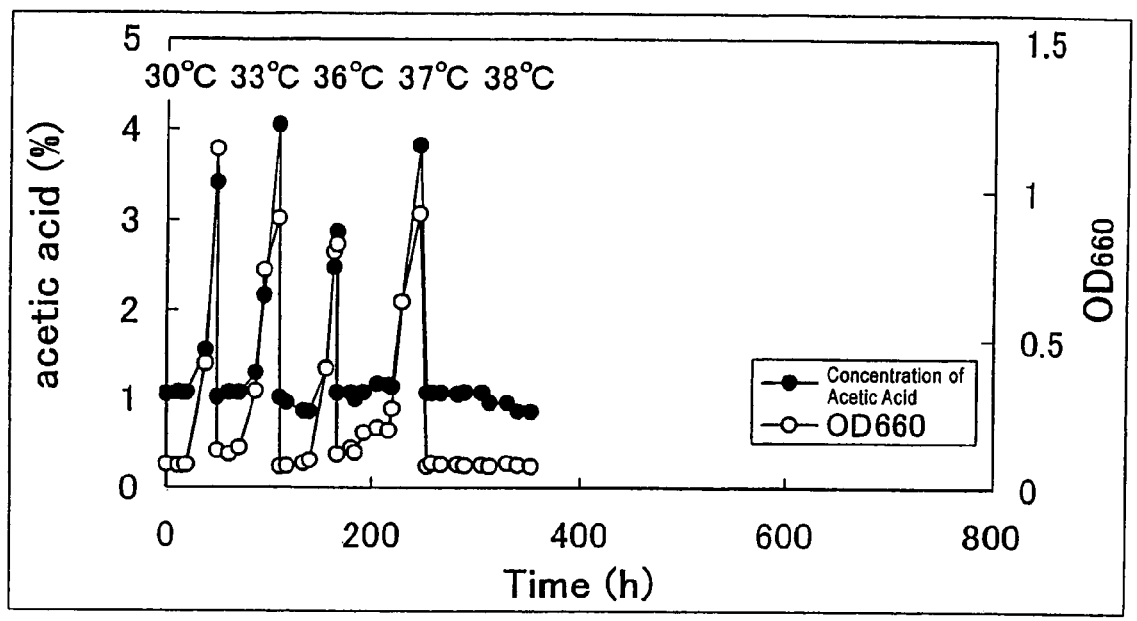
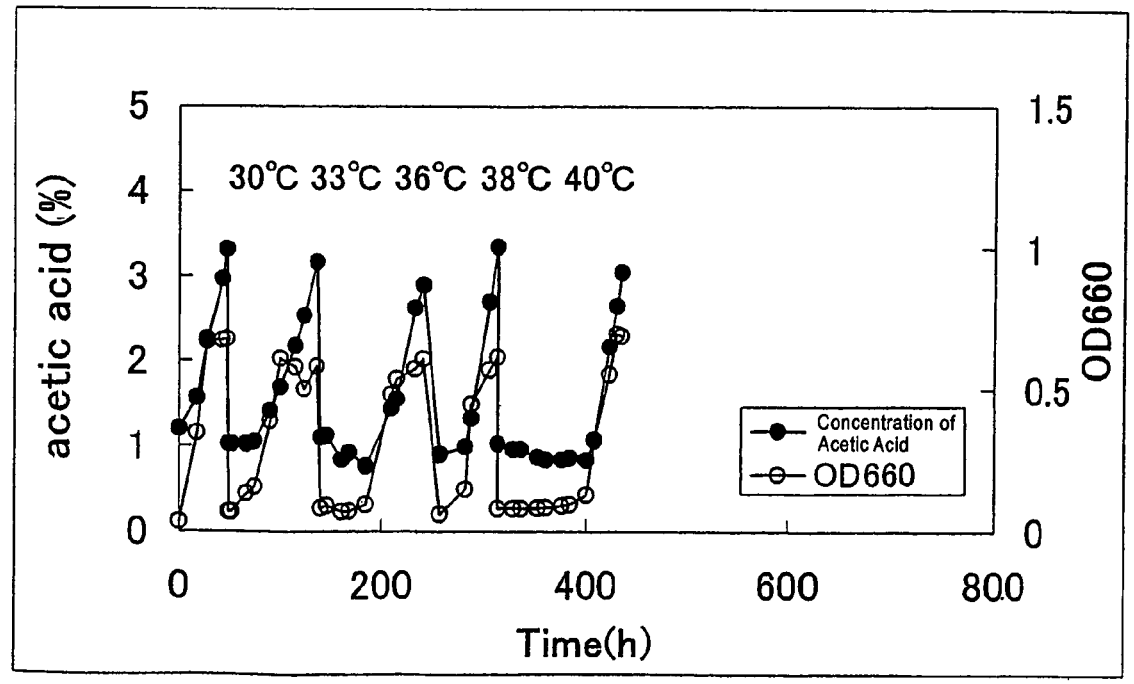

Figure 5

| | | |
|---|---|---|
| MetSerIlePheSerLysTyrGluGlyLeu | AlaSerAlaLeuSerAlaValThrAlaAsp | 20 |
| GlyGlyArgAsnProPheAsnValValIle | GluLysProIleSerSerThrValGlyLeu | 40 |
| IleGluGlyArgGluThrLeuLeuPheGly | ThrAsnAsnTyrLeuGlyLeuSerGlnSer | 60 |
| ProAlaAlaIleGluAlaAlaValGluAla | AlaArgAlaTyrGlyValGlyThrThrGly | 80 |
| SerArgIleAlaAsnGlyThrGlnGlyLeu | HisArgGlnLeuGluGluArgLeuCysThr | 100 |
| PhePheArgArgArgHisCysMetValPhe | SerThrGlyTyrGlnAlaAsnLeuGlyThr | 120 |
| IleSerAlaLeuAlaGlyLysAspAspTyr | LeuLeuLeuAspAlaAspSerHisAlaSer | 140 |
| IleTyrAspGlySerArgLeuGlyHisAla | GlnValIleArgPheArgHisAsnAspAla | 160 |
| AspAspLeuHisLysArgLeuArgArgLeu | AspGlyThrProGlyAlaLysLeuValVal | 180 |
| ValGluGlyIleTyrSerMetMetGlyAsp | ValValProMetAlaGluPheAlaAlaVal | 200 |
| LysArgGluThrGlyAlaTrpLeuLeuAla | AspGluAlaHisSerValGlyValMetGly | 220 |
| GluHisGlyArgGlyValAlaGluSerAsp | GlyValGluAspAspValAspPheValVal | 240 |
| GlyThrPheSerLysSerLeuGlyThrVal | GlyGlyTyrCysValSerAsnHisAlaGly | 260 |
| LeuAspLeuIleArgLeuCysSerArgPro | TyrMetPheThrAlaSerLeuProProGlu | 280 |
| ValIleAlaAlaThrMetAlaAlaLeuThr | GluLeuGluAsnArgProGluLeuArgVal | 300 |
| ArgLeuMetAspAsnAlaArgArgLeuHis | AspGlyLeuGlnAlaAlaGlyLeuArgThr | 320 |
| GlyProGlnAlaSerProValValSerVal | IleLeuAspAspValAlaValAlaValAla | 340 |
| PheTrpAsnArgLeuLeuAspLeuGlyVal | TyrValAsnLeuSerLeuProProAlaThr | 360 |
| ProAspGlnHisProLeuLeuArgThrSer | ValMetAlaThrHisThrProGluGlnIle | 380 |
| AspArgAlaValGluIlePheAlaValVal | AlaGlyGluMetGlyIleAsnArgAlaAla | 400 |

Figure 6

MetThrSerLeuPheSerLysPheGluGly ThrAlaGlyAlaLeuGlySerValValAla      20
ValGlyGlyArgAsnProPheAlaValVal IleGluLysProValSerSerThrValGly      40
IleIleGluGlyArgGluThrLeuLeuPhe GlyThrAsnAsnTyrLeuGlyLeuSerGln      60
SerLysAsnAlaIleGlnAlaAlaGlnGln AlaAlaAlaAlaCysGlyValGlyThrThr      80
GlySerArgIleAlaAsnGlyThrGlnSer LeuHisArgGlnLeuGluLysAspIleAla     100
AlaPhePheGlyArgArgAspAlaMetVal PheSerThrGlyTyrGlnAlaAsnLeuGly     120
IleIleSerThrLeuAlaGlyLysAspAsp HisLeuPheLeuAspAlaAspSerHisAla     140
SerIleTyrAspGlySerArgLeuSerAla AlaGluValIleArgPheArgHisAsnAsp     160
ProAspAsnLeuTyrLysArgLeuLysArg MetAspGlyThrProGlyAlaLysLeuIle     180
ValValGluGlyIleTyrSerMetThrGly AsnValAlaProIleAlaGluPheValAla     200
ValLysLysGluThrGlyAlaTyrLeuLeu ValAspGluAlaHisSerPheGlyValLeu     220
GlyGlnAsnGlyArgGlyAlaAlaGluAla AspGlyValGluAlaAspValAspPheVal     240
ValGlyThrPheSerLysSerLeuGlyThr ValGlyGlyTyrCysValSerAspHisPro     260
GluLeuGluPheValArgLeuAsnCysArg ProTyrMetPheThrAlaSerLeuProPro     280
GluValIleAlaAlaThrThrAlaAlaLeu LysAspMetGlnAlaHisProGluLeuArg     300
LysGlnLeuMetAlaAsnAlaGlnGlnLeu HisAlaGlyPheValAspIleGlyLeuAsn     320
AlaSerLysHisAlaThrProValIleAla ValThrLeuGluThrAlaGluGluAlaIle     340
ProMetTrpAsnArgLeuLeuGluLeuGly ValTyrValAsnLeuSerLeuProProAla     360
ThrProAspSerArgProLeuLeuArgCys SerValMetAlaThrHisThrProGluGln     380
IleAlaGlnAlaIleAlaIlePheArgGln AlaAlaAlaGluValGlyValThrIleThr     400
ProSerAlaAla

Figure 7

5'-CTGGCTGCCTGTATCGTCTCTCTCAAGCAG-3'

Figure 8

5'-ACGGCTGCAGCTGGTCTGCCTGCCGTATCT-3'

Figure 9

5'-GGCAAACCTCGGCATTATTTCCACGCTGGC-3'

Figure 10

5'-GCGAATCTGGTGTAGCCGGAGGAAGGCTG-3'

Figure 11

5'-GCCAGCGTGGAAATAATGCCGAGGTTTGCC-3'

Figure 12

5'-CAGCCTTCCTCCGGCTACACCAGATTCGC-3'

SEQUENCE LISTING

<160> NUMBER OF SEQ ID NOS: 10

<210> SEQ ID NO 1
<211> LENGTH: 2016
<212> TYPE: DNA
<213> ORGANISM: Gluconacetobacter entanii

<400> SEQUENCE: 1

```
gatatcaatg gcagcagcaa gatcgttgag gatctggcct ttgattcact ggccgtcatg      60
aattttgtca tggaaatcga ggacacgctc gacgtttccg tgccgcttga ccggctggct     120
gatatccgca ccattgatga tctggctgcc tgtatcgtct ctctcaagca ggcatcctga     180
tacaccatgt cgattttctc gaaatatgaa ggccttgcgt ccgccctgtc ggcggtaacg     240
gccgatggtg ggcgcaaccc gttcaacgtc gtgatcgaaa agcccatttc ctccacggtc     300
gggctgatcg aagggcgcga gacgcttctg ttcggcacca caactatct tgggctgagc      360 cagtccccgg ccgcgatcga agcggcggtg gaagccgcca gggcttatgg tgtcggcacg     420
accggatcgc gcatcgccaa tggcacgcag ggtctgcacc gccagttgga agagcggctg     480
tgcaccttct tccgtcgtcg gcactgcatg gtgttttcca ccggttacca ggccaatctg     540
ggcacgattt ccgcactggc gggcaaggac gattatctgc tgcttgatgc ggacagccat     600
gccagcatct atgatggcag ccgccttggc catgcgcagg tcatccgctt ccgtcacaac     660
gacgccgatg acctgcataa acgcctgcgc cgccttgatg gtacgcccgg agcgaaactg     720
gtcgtggtcg aaggcatcta ttccatgatg ggcgacgtcg ttcccatggc ggaattcgcg     780
gccgtcaagc gggaaaccgg tgcatggctg ctggcggatg aagcacattc cgttggtgta     840
atgggcgaac atggccgtgg cgtggcggaa tccgacggcg tggaagatga tgtcgatttt     900
gtcgtcggca ccttttccaa aagccttggc acggttggtg gctactgtgt ttccaaccat     960
gccgggctga acctgatccg gctgtgttcg cgtccgtaca tgttcaccgc atccctgccg    1020
ccggaagtca tcgccgcgac catggccgcg ctgactgaac tggaaaaccg gccggaactg    1080
```

-continued

```
cgcgtgcggt tgatggacaa tgcacgcagg cttcatgacg ggctgcaggc ggccggcctg      1140
cgcaccggcc cgcaggccag tcctgtcgtg tccgtcattc tggatgatgt ggcggttgcc      1200
gtggcgttct ggaaccggct gctggacctt ggggtttacg tcaacctcag cctgccgcct      1260
gcaacgcccg accagcatcc cctgctgcgg acctccgtca tggcgaccca tacgccggag      1320
cagatagacc gggccgtgga aatcttcgcc gttgtagcgg gcgagatggg tatcaaccgc      1380
gccgcctgaa aaacctgcc tgccgtaatt tccacagcag atacggcagg cagaccagcg       1440
gatgccgttc cgaaaacggc cccagcggca gttcaatgcc ggaatgccgc ctgatcttcc      1500
atgcgatata gcgcgcgcca ccttcaaacg tgaaggcccc cttgaacagg cggctgacat      1560
tcagcacgcg ccccagccga ccacgcagcc accagccttc gtacatcttc cggcgcagtt      1620
caggtgtcag ctgggggtt agttgatcgc cctcagaccg gaacggcagg ccatcggcgc       1680
gccatacatc cggcagcagg cgcctgtacc gtgcttcctg ccctgtagc aggctacgcg       1740 gcctgcggcc gttctccaca cgcagttccg caccgtaagt atgggcgaac agggccagcc      1800
agtagtcatc ggccgtgccc tgtgccggac ccagggcggc agcccagcgc ccgcctgcc       1860 ccaccgcgcg gataatgcag gccaggatgg catcggccgc gtccggttcc ctgacccata      1920
caagccgcac aggctggcag aagcgtgccc agaccgtggt atccaacgtg gcgcgtcccg      1980
tcatgcggcg gaactgcgct atggacagga tggcca                               2016
```

<210> SEQ ID NO 2
<211> LENGTH: 400
<212> TYPE: PRT
<213> ORGANISM: Gluconacetobacter entanii

<400> SEQUENCE: 2

```
Met Ser Ile Phe Ser Lys Tyr Glu Gly Leu Ala Ser Ala Leu Ser Ala
1               5                   10                  15

Val Thr Ala Asp Gly Gly Arg Asn Pro Phe Asn Val Val Ile Glu Lys
            20                  25                  30

Pro Ile Ser Ser Thr Val Gly Leu Ile Glu Gly Arg Glu Thr Leu Leu
        35                  40                  45

Phe Gly Thr Asn Asn Tyr Leu Gly Leu Ser Gln Ser Pro Ala Ala Ile
    50                  55                  60

Glu Ala Ala Val Glu Ala Ala Arg Ala Tyr Gly Val Gly Thr Thr Gly
65                  70                  75                  80

Ser Arg Ile Ala Asn Gly Thr Gln Gly Leu His Arg Gln Leu Glu Glu
                85                  90                  95

Arg Leu Cys Thr Phe Phe Arg Arg His Cys Met Val Phe Ser Thr
            100                 105                 110

Gly Tyr Gln Ala Asn Leu Gly Thr Ile Ser Ala Leu Ala Gly Lys Asp
        115                 120                 125

Asp Tyr Leu Leu Asp Ala Asp Ser His Ala Ser Ile Tyr Asp Gly
    130                 135                 140

Ser Arg Leu Gly His Ala Gln Val Ile Arg Phe Arg His Asn Asp Ala
145                 150                 155                 160

Asp Asp Leu His Lys Arg Leu Arg Arg Leu Asp Gly Thr Pro Gly Ala
                165                 170                 175

Lys Leu Val Val Val Glu Gly Ile Tyr Ser Met Met Gly Asp Val Val
            180                 185                 190

Pro Met Ala Glu Phe Ala Ala Val Lys Arg Glu Thr Gly Ala Trp Leu
        195                 200                 205
```

```
Leu Ala Asp Glu Ala His Ser Val Gly Val Met Gly Glu His Gly Arg
    210                 215                 220
Gly Val Ala Glu Ser Asp Gly Val Glu Asp Val Asp Phe Val Val
225                 230                 235                 240
Gly Thr Phe Ser Lys Ser Leu Gly Thr Val Gly Gly Tyr Cys Val Ser
                245                 250                 255
Asn His Ala Gly Leu Asp Leu Ile Arg Leu Cys Ser Arg Pro Tyr Met
                260                 265                 270
Phe Thr Ala Ser Leu Pro Pro Glu Val Ile Ala Ala Thr Met Ala Ala
            275                 280                 285
Leu Thr Glu Leu Glu Asn Arg Pro Glu Leu Arg Val Arg Leu Met Asp
    290                 295                 300
Asn Ala Arg Arg Leu His Asp Gly Leu Gln Ala Ala Gly Leu Arg Thr
305                 310                 315                 320
Gly Pro Gln Ala Ser Pro Val Val Ser Val Ile Leu Asp Asp Val Ala
                325                 330                 335
Val Ala Val Ala Phe Trp Asn Arg Leu Leu Asp Leu Gly Val Tyr Val
                340                 345                 350
Asn Leu Ser Leu Pro Pro Ala Thr Pro Asp Gln His Pro Leu Leu Arg
            355                 360                 365
Thr Ser Val Met Ala Thr His Thr Pro Glu Gln Ile Asp Arg Ala Val
    370                 375                 380
Glu Ile Phe Ala Val Val Ala Gly Glu Met Gly Ile Asn Arg Ala Ala
385                 390                 395                 400

<210> SEQ ID NO 3
<211> LENGTH: 1360
<212> TYPE: DNA
<213> ORGANISM: Acetobacter aceti

<400> SEQUENCE: 3
gaagacagct ggatgtatc tatcccgctc gacaaactgg ctgatatccg aacgattaat      60
gaccttgccg cttgcattgt tgctctgaaa acaaagggt gaggcgtgga tgacatcact     120
attttccaaa tttgaaggta cggcaggcgc gctgggttcc gttgtggccg taggcggtcg     180
caacccttt gctgttgtta ttgaaaaacc tgtctcttca actgttggaa ttattgaagg     240
tcgggaaacg cttcttttg gcaccaataa ctatttgggg cttagtcaat ccaaaaatgc     300
cattcaagca gcccagcagg ctgccgcggc atgtggcgta ggcacaacgg gctcacgcat     360
tgcaaatggc acacaatccc tgcaccgaca gcttgaaaaa gatattgccg cgttttttgg     420
tcggcgtgat gccatggttt tttccacggg gtatcaggca aacctcggca ttatttccac     480
gctggcaggt aaggatgacc acctgttct ggatgctgat agccacgcca gtatctatga     540
tgcagccgc ctgagtgcag cagaagttat tcgcttccgc cataatgatc cagacaacct     600
ttataaacgc cttaaacgca tggatggcac gccaggcgcc aaattgattg tggttgaagg     660
cattattcc atgacgggta atgttgcccc gattgcagaa tttgttgctg ttaaaaaaga     720
aacaggcgct tacctgctgg tagatgaagc ccattctttt ggcgtgttgg gtcaaaatgg     780
gcgtggtgcc gctgaggctg atggcgtgga agctgatgtg actttgttg tcggcacatt     840
ttccaaaagc ttgggcacag ttggcggtta ctgcgtatct gaccatcctg agctggagtt     900
tgtgcgctta aactgccggc cctatatgtt tacggcatcg ctaccgccgg aagttattgc     960
tgccacaacg gctgccttga agatatgca ggcacatcct gaattgcgta agcagcttat    1020
```

-continued

```
ggcaaacgcg cagcaactac atgcaggttt tgtagatatt gggctaaatg ccagcaaaca    1080
cgcaacccca gttattgccg ttacattgga acagctgaa gaagctattc ccatgtggaa     1140
caggcttttg aacttggtg tttatgtaaa tctcagcctt cctccggcta caccagattc     1200
gcggccgttg ctccgttgtt ccgtaatggc acccatacg cccgaacaaa ttgcgcaggc     1260
tattgccata ttcaggcagg ctgcggcaga agtaggcgta accatcacac cctccgctgc    1320
ttaaaaaaaa gctatttgcg cttgaatgcc ccttgctgcc                          1360

<210> SEQ ID NO 4
<211> LENGTH: 404
<212> TYPE: PRT
<213> ORGANISM: Acetobacter aceti

<400> SEQUENCE: 4

Met Thr Ser Leu Phe Ser Lys Phe Glu Gly Thr Ala Gly Ala Leu Gly
1               5                   10                  15

Ser Val Val Ala Val Gly Gly Arg Asn Pro Phe Ala Val Val Ile Glu
                20                  25                  30

Lys Pro Val Ser Ser Thr Val Gly Ile Ile Glu Gly Arg Glu Thr Leu
            35                  40                  45

Leu Phe Gly Thr Asn Asn Tyr Leu Gly Leu Ser Gln Ser Lys Asn Ala
        50                  55                  60

Ile Gln Ala Ala Gln Gln Ala Ala Ala Cys Gly Val Gly Thr Thr
65                  70                  75                  80

Gly Ser Arg Ile Ala Asn Gly Thr Gln Ser Leu His Arg Gln Leu Glu
                85                  90                  95

Lys Asp Ile Ala Ala Phe Phe Gly Arg Arg Asp Ala Met Val Phe Ser
            100                 105                 110

Thr Gly Tyr Gln Ala Asn Leu Gly Ile Ile Ser Thr Leu Ala Gly Lys
        115                 120                 125

Asp Asp His Leu Phe Leu Asp Ala Asp Ser His Ala Ser Ile Tyr Asp
130                 135                 140

Gly Ser Arg Leu Ser Ala Ala Glu Val Ile Arg Phe Arg His Asn Asp
145                 150                 155                 160

Pro Asp Asn Leu Tyr Lys Arg Leu Lys Arg Met Asp Gly Thr Pro Gly
                165                 170                 175

Ala Lys Leu Ile Val Val Glu Gly Ile Tyr Ser Met Thr Gly Asn Val
            180                 185                 190

Ala Pro Ile Ala Glu Phe Val Ala Val Lys Lys Glu Thr Gly Ala Tyr
        195                 200                 205

Leu Leu Val Asp Glu Ala His Ser Phe Gly Val Leu Gly Gln Asn Gly
    210                 215                 220

Arg Gly Ala Ala Glu Ala Asp Gly Val Glu Ala Asp Val Asp Phe Val
225                 230                 235                 240

Val Gly Thr Phe Ser Lys Ser Leu Gly Thr Val Gly Gly Tyr Cys Val
                245                 250                 255

Ser Asp His Pro Glu Leu Glu Phe Val Arg Leu Asn Cys Arg Pro Tyr
            260                 265                 270

Met Phe Thr Ala Ser Leu Pro Pro Glu Val Ile Ala Ala Thr Thr Ala
        275                 280                 285

Ala Leu Lys Asp Met Gln Ala His Pro Glu Leu Arg Lys Gln Leu Met
    290                 295                 300

Ala Asn Ala Gln Gln Leu His Ala Gly Phe Val Asp Ile Gly Leu Asn
305                 310                 315                 320
```

Ala Ser Lys His Ala Thr Pro Val Ile Ala Val Thr Leu Glu Thr Ala
                325                 330                 335

Glu Glu Ala Ile Pro Met Trp Asn Arg Leu Leu Glu Leu Gly Val Tyr
            340                 345                 350

Val Asn Leu Ser Leu Pro Pro Ala Thr Pro Asp Ser Arg Pro Leu Leu
        355                 360                 365

Arg Cys Ser Val Met Ala Thr His Thr Pro Gln Ile Ala Gln Ala
    370                 375                 380

Ile Ala Ile Phe Arg Gln Ala Ala Ala Glu Val Gly Val Thr Ile Thr
385                 390                 395                 400

Pro Ser Ala Ala

<210> SEQ ID NO 5
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: synthetic primer

<400> SEQUENCE: 5
ctggctgcct gtatcgtctc tctcaagcag                                    30

<210> SEQ ID NO 6
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: synthetic primer

<400> SEQUENCE: 6
acggctgcag ctggtctgcc tgccgtatct                                    30

<210> SEQ ID NO 7
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: synthetic primer

<400> SEQUENCE: 7
ggcaaacctc ggcattattt ccacgctggc                                    30

<210> SEQ ID NO 8
<211> LENGTH: 29
<212> TYPE: DNA
<213> ORGANISM: Artificial Sequence
<220> FEATURE:
<221> NAME/KEY: misc_feature
<222> LOCATION: (1)..(29)
<223> OTHER INFORMATION: synthetic primer

<400> SEQUENCE: 8
gcgaatctgg tgtagccgga ggaaggctg                                     29

<210> SEQ ID NO 9
<211> LENGTH: 30
<212> TYPE: DNA
<213> ORGANISM: Artificial Sequence

```
<220> FEATURE:
<221> NAME/KEY: misc_feature
<222> LOCATION: (1)..(30)
<223> OTHER INFORMATION: synthetic primer

<400> SEQUENCE: 9
gccagcgtgg aaataatgcc gaggtttgcc                                30

<210> SEQ ID NO 10
<211> LENGTH: 29
<212> TYPE: DNA
<213> ORGANISM: Artificial Sequence
<220> FEATURE:
<221> NAME/KEY: misc_feature
<222> LOCATION: (1)..(29)
<223> OTHER INFORMATION: synthetic primer

<400> SEQUENCE: 10
cagccttcct ccggctacac cagattcgc                                 29
```

GENE PARTICIPATING IN ACETIC ACID TOLERANCE, ACETIC ACID BACTERIA BRED USING THE GENE, AND PROCESS FOR PRODUCING VINEGAR WITH THE USE OF THE ACETIC ACID BACTERIA

TECHNICAL FIELD TO WHICH THE INVENTION PERTAINS

The present invention relates to genes that encode protein having a function of enhancing acetic acid tolerance derived from microorganisms, microorganisms whose copy numbers of the genes are amplified, particularly acetic acid bacteria which belong to the genus *Acetobacter* or the genus *Gluconacetobacter*, and a method of efficiently producing vinegar containing acetic acid at a high concentration by using these microorganisms.

PRIOR ART

Acetic acid bacteria are microorganisms widely used in producing vinegar, and particularly acetic acid bacteria which belong to the genus *Acetobacter* or the genus *Gluconacetobacter* are utilized for industrial acetic acid fermentation.

In acetic acid fermentation, ethanol in medium is oxidized to acetic acid by acetic acid bacteria, and acetic acid resultantly accumulates in the medium, but acetic acid is inhibitive for acetic acid bacteria as well, and growth ability and fermentation ability of acetic acid bacteria gradually decrease as the concentration of acetic acid in the medium increases.

Accordingly, it is required in acetic acid fermentation that growth ability and fermentation ability do not decrease even at higher concentration of acetic acid, i.e. development of acetic acid bacteria having strong acetic acid tolerance is required. It has been attempted as one of the means that genes participating in acetic acid tolerance (acetic acid resistance-genes) are cloned and acetic acid bacteria are bred and improved by using the acetic acid resistance-genes.

As for findings relating to acetic acid resistance-genes of acetic acid bacteria heretofore, three genes (aarA, aarB, and aarC) clustering have been cloned as complementary genes which can restore the acetic acid sensitive mutants of acetic acid bacteria belonging to the genus *Acetobacter*, to the original tolerance (see non-patent literature 1, for instance).

Among them, it was presumed that aarA gene encodes citric acid synthase and aarC gene encodes enzyme relating to assimilation of acetic acid, while the function of aarB gene has been uncertain (see non-patent literature 2, for instance).

In the transformants obtained by transformation with cloned gene fragment containing these three acetic acid resistance-genes on multi-copy plasmid to *Acetobacter aceti* subspecies xylinum IF03288 strain, the level of improvement of acetic acid tolerance was only low, and it was uncertain if ability of these three acetic acid resistance-genes in actual acetic acid fermentation was improved or not (see non-patent literature 1, for instance).

Meanwhile, there has been a disclosed example in which improvement of the final acetic acid concentration in acetic acid fermentation was confirmed by introducing gene encoding membrane-bound aldehyde dehydrogenase (ALDH) cloned from acetic acid bacteria into acetic acid bacteria (see non-patent literature 2, for instance). However, since ALDH is not an enzyme directly participating in acetic acid tolerance but that having a function of oxidizing aldehyde, it could not be concluded whether gene encoding ALDH was the exact acetic acid resistance-gene.

Patent Literature 1
  Japanese Laid-Open Patent Application No. 1991-219878

Patent Literature 2
  Japanese Laid-Open Patent Application No. 1990-2364

Patent Literature 3
  Japanese Laid-Open Patent Application No. 1985-9489

Patent Literature 4
  Japanese Laid-Open Patent Application No. 1985-9488

Non-patent Literature 1
  Journal of Bacteriology, vol. 172, 2096-2104, 1990

Non-patent Literature 2
  Journal of Fermentation and Bioengineering, vol. 76, 270-275, 1993

Non-patent Literature 3
  Applied of Environment and Microbiology, vol. 55, 171-176, 1989

Non-patent Literature 4
  Agricultural and Biological Chemistry, vol. 52, p. 3125-3129, 1988

Non-patent Literature 5
  Agricultural and Biological Chemistry, vol. 49, p. 2091-2097, 1985

Non-patent Literature 6
  Bioscience, Biotechnology and Biochemistry, vol. 58, p. 974-975, 1994

PROBLEM TO BE SOLVED BY THE INVENTION

As mentioned above, no example that has elucidated acetic acid tolerance of acetic acid bacteria on genetic level and has succeeded in the development of practical acetic acid bacteria having high acetic acid tolerance has been reported heretofore. However, development of acetic acid bacteria superior in acetic acid tolerance would allow the performance of acetic acid fermentation at higher concentration than that conventional one and efficient production of acetic acid at a high concentration and vinegar at a higher concentration. Therefore, the present inventors attempted again to elucidate the improvement of acetic acid tolerance of acetic acid bacteria on genetic level.

As a result of consideration from various aspects, and from the view point that it was important to obtain novel acetic acid resistance-genes encoding proteins that have a function capable of improving acetic acid tolerance on practical level and to breed acetic acid bacteria having stronger acetic acid tolerance with the use of the obtained acetic acid resistance-genes, the present inventors have newly set novel technical tasks to furnish novel genes participating in acetic acid tolerance derived from microorganisms belonging to acetic acid bacteria, and to furnish a method of improving acetic acid tolerance of microorganisms by using the genes, particularly a method of improving acetic acid tolerance of microorganisms belonging to acetic acid bacteria, further a method of efficiently producing vinegar having acetic acid at a high concentration by using the acetic acid bacteria whose acetic acid tolerance was improved.

MEANS FOR SOLVING PROBLEMS

The present inventors hypothesized that specific genes participating in acetic acid tolerance that do not exist in other microorganisms should exist in acetic acid bacteria capable of growing and fermenting even in the presence of acetic acid, and the present inventors obtained a novel concept that the use of these genes would allow improvement of acetic acid tolerance of microorganisms more than before, further it would allow the development of an efficient method of producing novel vinegar containing acetic acid at a high concentration which could not be conventionally obtained.

As for the conventional method of obtaining acetic acid resistance-genes, it was popular that genes which complement mutant of acetic acid bacteria with acetic acid sensitivity were cloned.

However, thinking that it was difficult to find acetic acid resistance-genes which were industrially useful by such a method, the present inventors have developed a method as that of finding acetic acid resistance-genes from acetic acid bacteria, in which chromosomal DNA library of acetic acid bacteria was constructed, this chromosomal DNA library was transformed into acetic acid bacteria, that can generally grow only under up to approximately 1% acetic acid and the genes capable of growing the strain in the presence of 2% acetic acid as well, were obtained by screening.

According to the use of this method, the present inventors have succeeded for the first time in cloning novel acetic acid resistance-genes that have a function of improving acetic acid tolerance on practical level from acetic acid bacteria belonging to the genus *Gluconacetobacter* practically used in producing vinegar.

Figure 1:
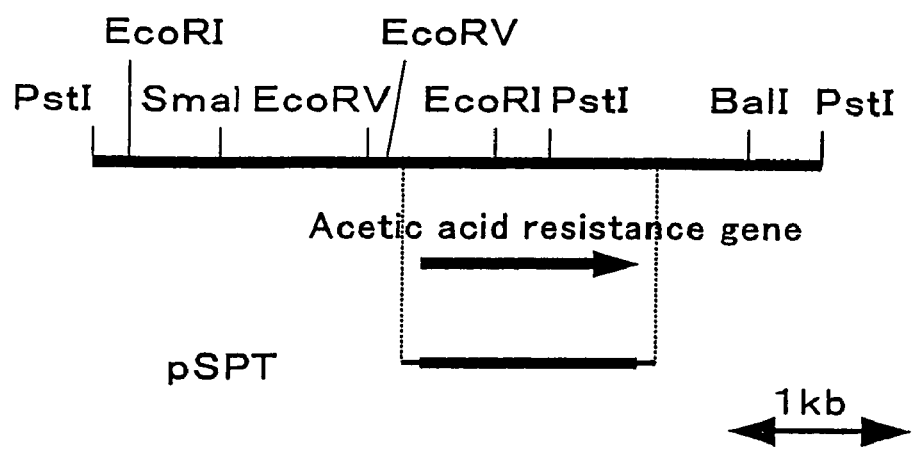
FIG. 1

This is a schematic view showing a restriction enzyme map of a gene fragment (pP1) derived from *Gluconacetobacter entanii* cloned by using PstI, the location of acetic acid resistance-gene and the insert into pSPT.

FIG. 2

This is a schematic view showing a restriction enzyme map of a gene fragment (pP2) derived from *Acetobacter aceti* cloned by using inverse PCR method, the location of acetic acid resistance-gene and an insert into pSPT2.

FIG. 3

This is a figure showing the time course in cultivation of the transformant whose copy numbers of acetic acid resistance-gene derived from *Gluconacetobacter entanii* were amplified.

FIG. 4

This is a figure showing the time course in acetic acid fermentation at higher temperature by the transformant whose copy numbers of acetic acid resistance-gene derived from *Gluconacetobacter entanii* were amplified.

FIG. 5

This is a figure showing an amino acid sequence (SEQ. ID No. 2) of the protein deduced by an acetic acid resistance-gene derived from *Gluconacetobacter entanii*.

FIG. 6

This is a figure showing an amino acid sequence (SEQ. ID No. 4) of the protein deduced by an acetic acid resistance-gene derived from *Acetobacter aceti*.

FIG. 7

This is a figure showing primer 1 which is described by the nucleotide sequence of SEQ. ID No.:5.

FIG. 8

This is a figure showing primer 2 which is described by the nucleotide sequence of SEQ. ID No.:6.

FIG. 9

This is a figure showing primer 3 which is described by the nucleotide sequence of SEQ. ID No.:7.

FIG. 10

This is a figure showing primer 4 which is described by the nucleotide sequence of SEQ. ID No.:8.

FIG. 11

This is a figure showing primer 5 which is described by the nucleotide sequence of SEQ. ID No.:9.

FIG. 12

This is a figure showing primer 6 which is described by the nucleotide sequence of SEQ. ID No.:10.

The obtained acetic acid resistance-genes showed homology with protein referred to as serine palmitoyltransferase that catalyze the first process of sphingolipid synthesis found in *Sphingomonas* and the like, and they were presumed as genes that encode serine palmitoyltransferases of acetic acid bacteria, as a result of homology search on DDBJ/EMBL/Genbank and SWISS-PROT/PIR.

However, the aforementioned gene of serine palmitoyltransferase from genus *Sphingomonas* was the only example in prokaryotes heretofore.

Further, one of the obtained serine palmitoyltransferase genes of acetic acid bacteria had 46.3% homology on amino acid sequence level with known serine palmitoyltransferase gene found in the genus *Sphingomonas* and it had approximately 25% homology with that of mice, the ratio of which were so low that it was confirmed that it was similar to other serine palmitoyltransferase genes to some extent, but it was novel gene encoding the novel protein (it is sometimes referred to as protein SPT) specific to acetic acid bacteria.

In addition, in the transformants in which the genes were inserted to plasmid vectors and transformed into acetic acid bacteria and their copy numbers were amplified, remarkable improvement in acetic acid tolerance could be seen. When the transformants were subjected to aerobic cultivation in the presence of ethanol, we found that growth rate and production rate were improved as well as growth lag time was shortened, further final acetic acid concentration was remarkably improved as a result. The present inventors further have succeeded in determination of the nucleotide sequence and the deduced amino acid sequence of genetic DNA encoding thereof. According to these findings, we have completed the present invention.

DISCLOSURE OF THE INVENTION

The embodiment of the present invention is as follows.

(1) A protein SPT described in following (A) or (B):
  (A) A protein having an amino acid sequence shown in SEQ. ID No. 2 in the sequence listing.
  (B) A protein consisting of an amino acid sequence comprising substitution, deletion, insertion, addition, or inversion of one or several amino acids in an amino acid sequence shown in SEQ. ID No. 2 in the sequence listing and having a function of enhancing acetic acid tolerance.

(2) A DNA of a gene encoding the protein SPT described in following (A) or (B):
  (A) A protein having an amino acid sequence shown in SEQ. ID No. 2 in the sequence listing.
  (B) A protein consisting of an amino acid sequence comprising substitution, deletion, insertion, addition, or inversion of one or several amino acids in an amino acid sequence shown in SEQ. ID No. 2 in the sequence listing and having a function of enhancing acetic acid tolerance.

(3) The DNA of a gene according to (2), that is a DNA described in following (a) or (b):
  (a) A DNA that comprises a nucleotide sequence consisting of nucleotides 187 to 1386 shown in SEQ. ID No. 1 in the sequence listing within the nucleotide sequence.
  (b) A DNA that hybridizes with a probe comprising a nucleotide sequence consisting of nucleotides 187 to 1386 shown in SEQ. ID No. 1 in the sequence listing within the nucleotide sequence or a part thereof under a stringent condition, and encodes protein having a function of enhancing acetic acid tolerance.

(4) A protein SPT2 described in following (A) or (B):
  (A) A protein having an amino acid sequence shown in SEQ. ID No. 4 in the sequence listing.
  (B) The protein SPT2 consisting of an amino acid sequence comprising substitution, deletion, insertion, addition, or inversion of one or several amino acids in an amino acid sequence shown in SEQ. ID No. 4 in the sequence listing and having a function of enhancing acetic acid tolerance.

(5) A DNA of a gene encoding the protein SPT2 described in following (A) or (B):
  (A) A protein having an amino acid sequence shown in SEQ. ID No. 4 in the sequence listing.
  (B) The protein SPT2 consisting of an amino acid sequence comprising substitution, deletion, insertion, addition, or inversion of one or several amino acids in an amino acid sequence shown in SEQ. ID No. 4 in the sequence listing and having a function of enhancing acetic acid tolerance.

(6) The DNA of a gene according to (5), that is a DNA described in following (A) or (B):
  (A) A DNA that comprises a nucleotide sequence consisting of nucleotides 110 to 1321 shown in SEQ. ID No. 3 in the sequence listing within the nucleotide sequence.
  (B) A DNA that hybridizes with a probe generated from a nucleotide sequence consisting of nucleotides 110 to 1321 shown in SEQ. ID No. 3 in the sequence listing within the nucleotide sequence or a part thereof under a stringent condition, and encodes protein having a function of promoting growth rate.

(7) Microorganisms wherein acetic acid tolerance thereof is enhanced by amplifying an intracellular copy number of the DNA according to any one of said (2), (3), (5), or (6).

(8) The microorganisms according to said (7), wherein the microorganisms are acetic acid bacteria belonging to the genus *Acetobacter* or the genus *Gluconacetobacter*.

(9) A method of producing vinegar, wherein microorganisms having alcohol oxidation ability among the microorganisms according to said (7) or (8), are cultured on medium containing alcohol and they produce and accumulate acetic acid in the medium, and a novel vinegar obtained therefrom whose acetic acid content is high (10-17.5%).

(10) A recombinant plasmid pUSPT (FERM BP-7932) including the DNA according to said (2) or (3), or a recombinant plasmid pUSPT2 (FERM BP-8304) including the DNA according to said (5) or (6).

(11) A recombinant plasmid comprising a DNA fragment having at least a nucleotide sequence shown in SEQ. ID No. 1 or 3, for instance plasmid pSPT or plasmid pSPT2 obtained from inserting these DNA fragments to an acetic acid bacteria-*Escherichia coli* shuttle vector (a multi-copy vector) pMV24, and/or a transformant which is obtained by introducing these plasmids pSPT and pSPT2 into *Acetobacter aceti* No. 1023 (FERM BP-2287) or *Acetobacter altoacetigenes* MH-24 strain (FERM BP-491).

By the present invention, tolerance against acetic acid can be provided toward microorganisms. Moreover, in microorganisms having alcohol oxidation ability, particularly in acetic acid bacteria, tolerance against acetic acid can be remarkably improved and the ability of efficiently accumulating acetic acid at a high concentration in the media can be provided.

BEST MODE FOR CARRYING OUT THE INVENTION

The present invention will be explained in more detail.

(1) The DNA of the Present Invention

The DNA of the present invention comprises homology with serine palmitoyltransferase of the genus *Sphingomonas* to some extent, and a nucleotide sequence that can encode protein having a function of improving acetic acid tolerance and comprising an amino acid sequence shown in SEQ. ID No. 2 in the sequence listing, and it comprises regulating elements and the structural gene.

The DNA of the present invention can be obtained from chromosomal DNA of *Gluconacetobacter entanii* as follows.

First, chromosomal DNA library of *Gluconacetobacter entanii*, for instance *Acetobacter altoacetigenes* MH-24 strain (deposited as FERM BP-491 with International Patent Organism Depositary) is prepared. Meanwhile chromosomal DNA is obtained by the method disclosed in patent literature 3.

Next, a chromosomal DNA library is prepared in order to isolate acetic acid resistance-genes from the obtained chromosomal DNA. To begin with, the chromosomal DNA is partially digested by suitable restriction enzymes to obtain various DNA fragment-mixtures. Various kinds of restriction enzymes can be used by adjusting cleavage reaction time and the like to control the extent of cleavage. For instance, chromosomal DNA is digested by the restriction enzyme of Sau3AI at the 30° C. or higher, preferably 37° C., at enzyme concentration of 1-10 units/ml for various time periods (1 min-2 h). Meanwhile, PstI was used in after-mentioned Examples.

Then digested fragments of chromosomal DNA are ligated to vector DNA that can replicate autonomously in acetic acid bacteria to prepare recombinant DNA. Specifically, this vector DNA is completely digested by the action of a restriction enzyme which yields a terminal nucleotide sequence complementary to the PstI restriction enzyme used for digesting of chromosomal DNA, for instance PstI, under the condition at the temperature of 30° C. and enzyme concentration of 1-100 units/ml for 1 h or longer.

Subsequently, the obtained chromosomal DNA fragment-mixtures in the above-mentioned manner are mixed with the digested vector DNA, then recombinant DNA is obtained by the action of T4DNA ligase to the mixture under the condition at the temperature of 4-16° C., at enzyme concentration of 1-100 units/ml for 1 h or longer, preferably 6-24 h.

Using the obtained recombinant DNA, acetic acid bacteria generally incapable of growing in the presence of acetic acid at higher than 1% concentration on agar media, for instance *Acetobacter aceti* No. 1023 strain (deposited as FERM BP-2287 with International Patent Organism Depositary) are transformed, and cultivated on agar media containing 2% acetic acid. DNA fragments including acetic acid resistance-genes can be obtained by cultivating there generated colonies into liquid media, then recovering plasmids from the obtained bacterial cells.

As for the DNA of the present invention, DNA comprising a nucleotide sequence shown in SEQ. ID No. 1 or 3 in the sequence listing is specifically exemplified, among which the nucleotide sequence consisting of nucleotides 187 to 1386 shown in SEQ. ID No. 1 within the nucleotide sequence or nucleotides 110 to 1321 shown in SEQ. ID No. 3 within the nucleotide sequence is coding region.

As the result of homology search on DDBJ/EMBL/Genbank and SWISS-PROT/PIR about the nucleotide sequence shown in SEQ. ID No. 1, an amino acid sequence shown in SEQ. ID No. 2 (FIG. 3: corresponding to nucleotides 187 to 1386), the nucleotide sequence shown in SEQ. ID No. 3 or an amino acid sequence shown in SEQ. ID No. 4 (FIG. 4: corresponding to nucleotides 110 to 1321), the nucleotide sequence shown in SEQ. ID No. 1 or the amino acid sequence shown in SEQ. ID No. 2 showed 46.3% homology with SPT1 gene of *Sphingomonas paucimobilis*, while showed 26.3% and 24.8% homologies with LCB1 gene and LCB2 gene of mice, respectively on amino acid sequence level, and the genes were presumed as those encoding serine palmitoyltransferases, but each of their homologies was as low as 50% or less, so that it was apparent that this was novel and different from these genes.

Further, the nucleotide sequence shown in SEQ. ID No. 2 or the amino acid sequence shown in SEQ. ID No. 4 showed 46.7% homology with SPT1 gene, while showed 22.6% and 19.8% homologies with LCB1 gene and LCB2 gene of mice, respectively on amino acid sequence level, and the genes were presumed as those of encoding serine palmitoyltransferases, but each of their homologies was as low as 50% or less and it was apparent that this was novel and different from these genes.

Meanwhile, it has been unknown at all that aforementioned SPT gene and the like participate in acetic acid tolerance.

Further, the DNA of the present invention was identified that it is a novel gene having a function of enhancing the acetic acid tolerance which is different from previously obtained acetic acid resistance-genes (aarA, aarB and aarC) of acetic acid bacteria, ADH gene having a function of enhancing acetic acid tolerance or the like.

As the nucleotide thereof was revealed, for instance the DNA of the present invention can also be obtained by polymerase chain reaction (PCR reaction) using genomic DNA of the acetic acid bacteria *Gluconacetobacter entanii* as a template and oligonucleotide synthesized based on the nucleotide sequence as a primer, or by hybridization using oligonucleotide synthesized based on the nucleotide sequence as a probe, as well.

As for the synthesis of the oligonucleotide, it can be synthesized, for instance using commercially available various DNA synthesizers in the conventional manner. In addition, PCR reaction can be performed in the conventional manner using Thermal Cycler Gene Amp PCR System 2400 (Applied Biosystems) and Taq DNA polymerase (Takara Shuzo Co., LTD.), KOD-Plus—(TOYOBO Co., LTD.) and the like.

As for the DNA encoding the protein having a function of enhancing acetic acid tolerance of the present invention, it may be a DNA encoding protein where one or several amino acid is deleted, substituted, inserted or added at one or several sites, as long as the function of enhancing acetic acid tolerance of the encoded protein is not impaired.

The DNA encoding a protein substantially identical to such protein having a function of enhancing acetic acid tolerance, can also be obtained by modifying the nucleotide sequence so that amino acid at a particular site is deleted, substituted, inserted or added by site-directed mutagenesis, for instance. Further, the modified DNA such as aforementioned one can also be obtained by conventionally known mutagenesis treatments.

In addition, as an amino acid sequence of protein and a nucleotide sequence encoding thereof are generally known that they are slightly different among species, strains, mutants, and variants, the DNA encoding substantially identical proteins can be obtained from general acetic acid bacteria, among which, species, strains, mutants and variants of the genus *Acetobacter* or the genus *Gluconacetobacter*.

Specifically, DNA encoding a protein substantially identical to the protein can be obtained from acetic acid bacteria belonging to the genus *Acetobacter* or the genus *Gluconacetobacter*, acetic acid bacteria belonging to the genus *Acetobacter* or the genus *Gluconacetobacter* treated for mutagenesis, or natural mutants or variants thereof, by for instance, isolating DNA: hybridizing under a stringent condition with DNA comprising a nucleotide sequence consisting of nucleotides 187 to 1386 shown in SEQ. ID No. 1 in the sequence listing within the nucleotide sequence or with DNA comprising a nucleotide sequence consisting of nucleotides 110 to 1321 shown in SEQ. ID No. 3 in the sequence listing within the nucleotide sequence, and DNA: encoding protein having a function of enhancing acetic acid tolerance. The term stringent condition here is a condition in which so-called specific hybrid is formed while non-specific hybrid is not formed. Though it is difficult to quantify this condition clearly, if one example is taken, a condition in which DNA having high homology, for instance DNA having homology of 70% or more hybridizes, while DNA having homology lower than that does not hybridize, or a condition in which general washing is performed for hybridization, for instance the washing is performed with 0.1% SDS at the salt concentration equivalent to 1×SSC at 60° C., can be exemplified.

(2) The Acetic Acid Bacteria of the Present Invention

The acetic acid bacteria of the present invention mean bacteria belonging to the genus *Acetobacter* or the genus *Gluconacetobacter*, or such bacteria, belonging to the genus *Acetobacter* or the genus *Gluconacetobacter* which are enhanced their acetic acid tolerance.

In bacteria belonging to the genus *Acetobacter, Acetobacter aceti* can be cited specifically, and *Acetobacter aceti* No. 1023 strain (deposited as FERM BP-2287 with International Patent Organism Depositary) can be exemplified.

Further, as for bacteria belonging to the genus *Gluconacetobacter, Gluconacetobacter entanii* can be cited, and *Acetobacter altoacetigenes* MH-24 strain currently deposited as FERM BP-491 with International Patent Organism Depositary can be exemplified.

Acetic acid tolerance can be enhanced, for instance, by amplifying intracellular copy numbers of acetic acid resistance-genes, or transforming bacteria belonging to the genus *Acetobacter* by using recombinant DNA obtained by ligated DNA fragments containing structural genes to promoter sequences that function efficiently in the bacteria belonging to the genus *Acetobacter*.

In addition, acetic acid tolerance can also be enhanced by replacing the promoter sequence of the genes on chromosomal DNA with other promoter sequence derived from microorganisms functioning efficiently in bacteria belonging to the genus *Acetobacter* or the genus *Gluconacetobacter*, for instance such promoters of other than acetic acid bacteria including ampicillin-resistance gene for plasmid pBR322, kanamycin-resistance gene for plasmid pACYC177, and chloramphenicol-resistance gene for plasmid pACYC184, β-galactosidase gene and the like from *Escherichia coli*.

Amplification of intracellular copy numbers of the genes can be conducted by introducing multi-copy vectors retaining the genes into cells of bacteria belonging to the genus *Acetobacter*, i.e. it can be conducted by introducing plasmid, transposon and the like retaining the genes into cells of bacteria belonging to the genus *Acetobacter* or the genus *Gluconacetobacter*.

As for multi-copy vectors, pMV24 (see non-patent literature 3, for instance), pTA5001 (A), pTA5001 (B) (see patent literature 4, for instance) and the like can be exemplified, and pMVL1 which is a chromosome-integrative type vector (see non-patent literature 4, for instance) can also be cited. Further, as for transposons, Mu, IS1452 and the like can be exemplified.

Transformation of DNA into acetic acid bacteria belonging to the genus *Acetobacter* or the genus *Gluconacetobacter* can be performed by calcium chloride method (see non-patent literature 5, for instance), electroporation method (see non-patent literature 6, for instance) and the like.

Enhancement of acetic acid tolerance in acetic acid bacteria belonging to the genus *Acetobacter* or the genus *Gluconacetobacter* having alcohol oxidation ability in the above-described manner, enables increase of the amount of production and production efficiency of acetic acid.

(3) Method of Producing Vinegar

Bacteria belonging to the genus *Acetobacter* or the genus *Gluconacetobacter*, which are selectively enhanced their acetic acid tolerance by amplification of copy numbers of acetic acid resistance-genes in the above-described manner, and which have alcohol oxidation ability, are cultured on media containing alcohol, and acetic acid is produced and accumulated in the media. Vinegar can be thus efficiently produced.

The acetic acid fermentation in the method of producing of the present invention may be performed in the same manner as the conventional method of producing vinegar by a method of fermentation by acetic acid bacteria. As for the medium used in acetic acid fermentation, it may be either synthetic medium or natural medium as long as they are containing carbon source, nitrogen source, inorganic substance and ethanol, and containing suitable amount of source of nutrition required by the used bacteria strain for its growth if it is needed.

As for carbon sources, various kinds of carbohydrates including glucose, sucrose and various kinds of organic acids, can be exemplified. As for nitrogen source, natural nitrogen source such as peptone, degradation product of the microorganisms and the like can be exemplified.

In addition, static culture, shaking culture, aeration-agitation culture and the like under aerobic condition are carried out, generally at the culture temperature of 30° C. The pH of medium is generally within the range of 2.5-7, preferably within the range of 2.7-6.5, and it also can be adjusted with various kinds of acids, various kinds of bases, buffers and the like. Generally, after cultivation of 1 to 21 days acetic acid is accumulated at a high concentration in the medium.

(4) Embodiment of the Present Invention

Further, as recombinant plasmids pUSPT and pUSPT2 which are made by inserting ORF relating to the present invention or acetic acid resistance-gene comprising thereof (SEQ. ID No. 1 or SEQ. ID No. 3) into *Escherichia coli* vector (multi-copy vector) pUC19, i.e. pUSPT has been deposited as FERM BP-7932 with International Patent Organism Depositary, National Institute of Advanced Industrial Science and Technology, Tsukuba Central 6, 1-1-1 Higashi, Tsukuba, Ibaraki, Japan since Mar. 1, 2002, and pUSPT2 has been deposited as FERM BP-8304 with International Patent Organism Depositary, National Institute of Advanced Industrial Science and Technology, Tsukuba Central 6, 1-1-1 Higashi, Tsukuba, Ibaraki, Japan since Feb. 26, 2003, so that DNA relating to the present invention can be available without difficulty, and a person skilled in the art would easily carry out the present invention. In addition, if it is desired, by using these recombinant plasmids, ORF relating to the present invention or acetic acid resistance-genes comprising thereof, are transferred to the vectors capable of replicating autonomously in acetic acid bacteria, and these are introduced into acetic acid bacteria and cultivated. By this procedure, vinegar having high acetic acid content, can be easily produced.

Still further, as explained above and as it is also apparent from after-mentioned examples, deposit of source of acetic acid resistance-genes, embodiment of PCR, preparation of plasmid vectors and recombinant plasmids, deposit of host bacteria and the like, have been elucidated, and each of them can be obtained, operated and processed easily, therefore, performance of each operation and treatment according to Examples leads to obtainment of the objected acetic acid tolerance-transformants. The use of them enables to produce acetic acid at a high concentration. Consequently, the present invention can be easily carried out in this point of view, as well.

The present invention will be explained more specifically with examples below.

EXAMPLE

Example 1

Cloning of Acetic Acid Resistance-Genes from *Gluconacetobacter entanii* and Determination of the Nucleotide Sequence and the Deduced Amino Acid Sequence (1) Generation of Chromosomal DNA Library

*Acetbacter altoacetigenes* MH-24 strain (FERMBP-491), that is one strain of *Gluconacetobacter entanii* was performed shaking culture at 30° C. on YPG medium (3% glucose, 0.5% yeast extract, and 0.2% polypeptone) added 6% acetic acid and 4% ethanol. After the cultivation, culture medium was centrifuged (7,500×g, 10 min) and bacterial cells were obtained. Chromosomal DNA was prepared from the obtained bacterial cells by the method disclosed in patent literature 3.

The obtained chromosomal DNA as explained above was partially digested by restriction enzyme PstI (Takara Shuzo Co., LTD.), further the *Escherichia coli*-acetic acid bacteria shuttle vector pMV24 was completely digested by restriction enzyme PstI. These types of DNA were mixed by adequate dose, ligated by using ligation kit (TaKaRa DNA Ligation Kit Ver. 2, Takara Shuzo Co., LTD.), and chromosomal DNA library of *Gluconacetobacter entanii* was constructed.

(2) Cloning of Acetic Acid Resistance-Genes

The chromosomal DNA library of *Gluconacetobacter entanii* obtained as explained above, was transformed into *Acetobacter aceti* No. 1023 strain (FERM BP-2287) that generally can grow only under up to approximately under 1% acetic acid concentration on agar medium.

Subsequently, transformed *Acetobacter aceti* No. 1023 strain was cultured for 4 days at 30° C. on YPG agar medium containing 2% acetic acid and 100 μg/ml of ampicillin.

When colonies generated on the agar medium were inoculated into YPG medium containing 100 μg/ml of ampicillin and cultured, and plasmids were recovered from the obtained bacterial cells, the plasmid in which PstI fragment of approximately 4 kbp was inserted, could be recovered as shown in FIG. 1 and this plasmid was named pP1. Further, it was confirmed that DNA fragment which enable *Acetobacter aceti* No. 1023 strain to grow on YPG agar medium containing 2% acetic acid, was approximately 2 kbp of EcoRV-BalI fragment in approximately 4 kbp of PstI fragment cloned into pP1.

The acetic acid resistance-gene fragment that enable to grow *Acetobacter aceti* No. 1023 strain on the agar medium containing 2% acetic acid, which strain usually can only be grown on agar medium containing up to approximately 1% acetic acid concentration, was thus obtained.

(3) Determination of the Nucleotide Sequence of Cloned DNA Fragment

The cloned EcoRV-BalI fragment mentioned above was inserted into SmaI site of pUC19, and the nucleotide sequence of the fragment was determined by Sanger's dideoxy chain-termination method, and the nucleotide sequence described in SEQ. ID No. 1 was determined consequently. Sequencing was conducted in the all domains of the both strands of DNA, and it was also conducted so that cleavage sites were overlapped.

The presence of open reading frame (ORF) encoding 400 of amino acids (FIG. 3), as shown in SEQ. ID No. 2, was confirmed in nucleotides 187 to 1386 of SEQ. ID No. 1.

Example 2

Enhancement of Acetic Acid Tolerance in Transformant, Transformed with Acetic Acid Resistance-Gene Derived from *Gluconacetobacter entanii*

(1) Transformation of *Acetobacter aceti*

Acetic acid resistance-gene derived from *Acetobacter altoacetigenes* MH-24 strain (FERM BP-491) cloned as explained above, was amplified by PCR method with KOD-Plus—(TOYOBO Co., LTD.), and plasmid pSPT in which the amplified DNA fragment was inserted into restriction enzyme SmaI cleavage site of the acetic acid bacteria-*Escherichia coli* shuttle vector pMV24 (see non-patent literature 3, for instance), was constructed. The outline of amplified fragment inserted into pSPT is shown in FIG. 1.

PCR method was performed as follows; i.e. PCR method was performed using genomic DNA derived from above-mentioned acetic acid bacterium as template and using primer 1 (the nucleotide sequence thereof is shown in SEQ. ID No. 5 (FIG. 7)) and primer 2 (the nucleotide sequence thereof is shown in SEQ. ID No. 6 (FIG. 8)) as primer in the following condition.

PCR method was performed i.e. for 30 cycles, in which 1 cycle is consisting of performance at 94° C. for 15 sec, 60° C. for 30 sec, and 68° C. for 2 min.

This pSPT was transformed into *Acetobacter aceti* No. 1023 strain by electoroporation method (see non-patent literature 6, for instance). The transformants were selected on YPG agar medium added 100 μg/ml of ampicillin and 2% acetic acid.

Plasmid was extracted from the transformant having ampicillin resistance grown on the selection medium in the conventional manner for analysis and it was confirmed that it retained the plasmid having acetic acid resistance-gene.

(2) Acetic Acid Tolerance of the Transformant

The ampicillin-resistant transformant having plasmid pSPT obtained as explained above was compared their growth on YPG medium added acetic acid to that of the original strain of *Acetobacter aceti* No. 1023 strain introduced only shuttle vector pMV24.

Specifically, the transformant including pSPT and the original strain having shuttle vector pMV24 were inoculated into 100 ml of YPG medium containing 3% ethanol and 100 μg/ml of ampicillin and into 100 ml of YPG medium containing 3% ethanol, 3% acetic acid and 100 μg/ml of ampicillin, respectively, and shaking culture (150 rpm) was performed at 30° C., and growth of the transformant in the medium containing acetic acid was compared to that of the original strain by measuring absorbance at 660 nm.

Figure 2:
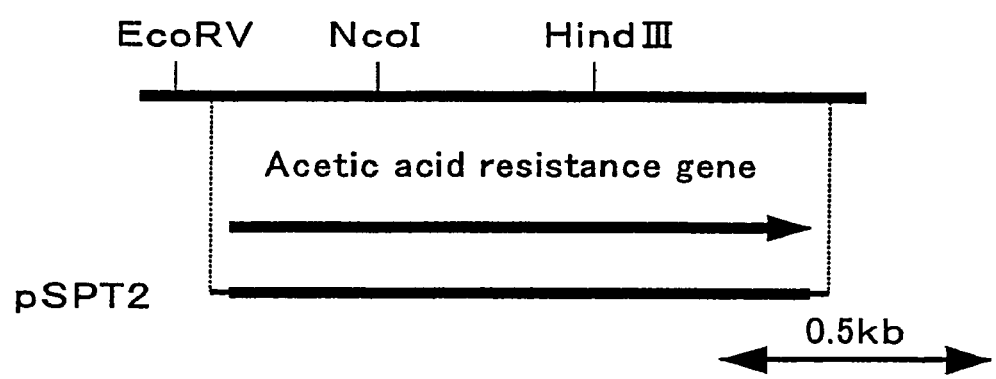

Consequently, it was confirmed that the transformant and the original strain *Acetobacter aceti* No. 1023 could grow almost similarly in the medium without containing acetic acid, while the transformant could grow but the original strain could not grow in the medium containing 3% acetic acid and 3% ethanol, as shown in FIG. 2. Function of enhancing acetic acid tolerance of acetic acid resistance-gene was confirmed.

(3) Thermal Resistance of the Transformant

The ampicillin-resistant transformant having plasmid pSPT obtained in above-mentioned (1), was compared their growth on YPG medium in which the cultivation temperature was changed, to that of the original strain of *Acetobacter aceti* No. 1023 introduced only shuttle vector pMV24.

Specifically, they were cultured with agitation rate at 400 rpm, aeration rate at 0.2 vvm and temperature of 30° C. in 1 L of YPG medium containing 1% acetic acid, 4% ethanol, and 100 μg/ml of ampicillin using 2 L of mini-jar fermenter (Chiyoda Seisakusho Co., LTD.: TBR-2-1), and fermented up to approximately 3% acetic acid concentration. Then, the culture medium was withdrawn from the mini-jar fermenter with 200 ml of it left, 800 ml of YPG medium containing acetic acid, ethanol and 100 μg/ml of ampicillin was newly added, it was adjusted to the concentration of 4% ethanol and 1% acetic acid, culture temperature was risen to 33° C., and fermentation was thus restarted.

When fermentation further progressed and concentration of acetic acid in the medium became approximately 3%, the culture medium was withdrawn again and the medium was added again, further culture temperature was risen to 36° C. to ferment them similarly, and still further acetic acid fermentation was performed by raising temperature 1° C. at a time in the same manner.

Then, growth of bacteria was compared by measuring absorbance at 660 nm, and the ratio of acetic acid fermentation was compared by measuring acetic acid concentration in culture medium.

Figure 3:
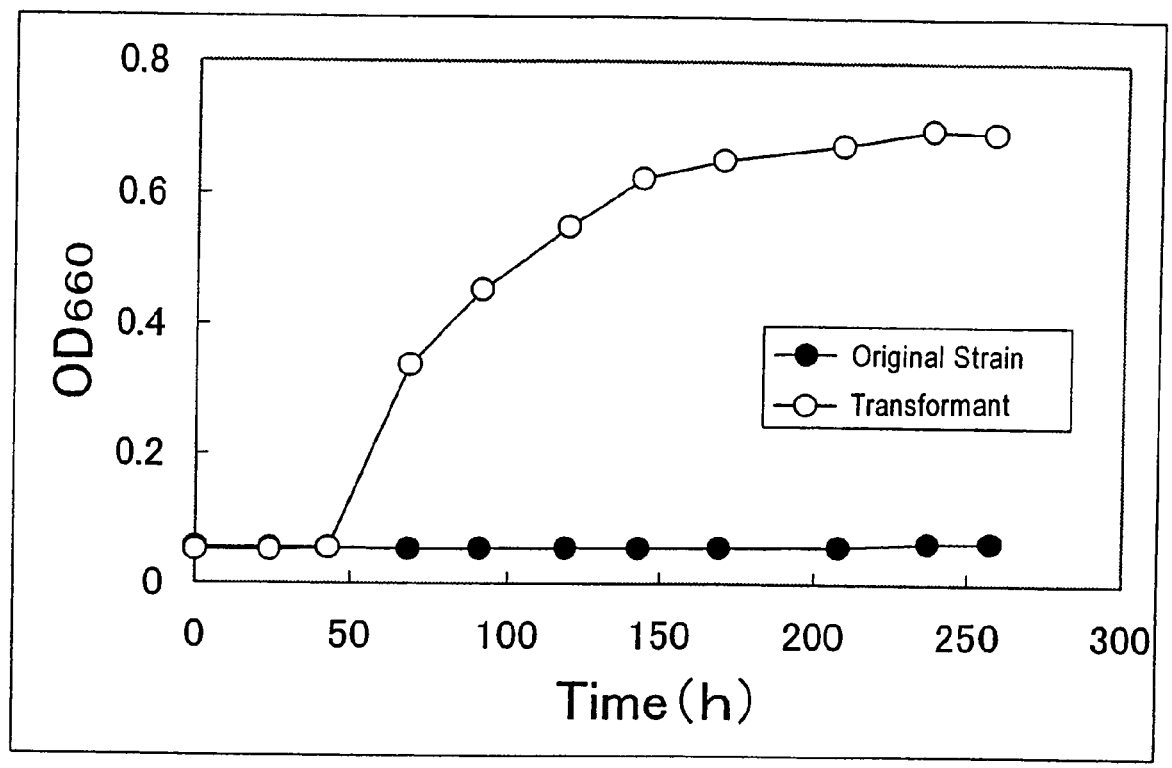

As a result, acetic acid fermentation and growth of bacteria at 40° C. were possible in the transformant, while acetic acid fermentation and growth of bacteria could confirmed only up to 37° C. in the original strain of *Acetobacter aceti* No. 1023 as shown in FIG. 3, and the function of enhancing acetic acid tolerance of SPT gene was confirmed.

Example 3

Acetic Acid Fermentation of the Transformant Transformed with Acetic Acid Resistance-Gene Derived from *Gluconacetobacter entanii*

The ampicillin-resistant transformant having plasmid pSPT obtained in Example 2 was compared with fermentation ability to that of the original strain of *Acetobacter aceti* No. 1023 having only shuttle vector pMV24.

Specifically, they were cultured with agitation rate at 400 rpm, aeration rate at 0.20 vvm and temperature of 30° C. in 2.5 L of YPG medium containing 1% acetic acid, 4% ethanol and 100 µg/ml of ampicillin using 5L of mini-jar fermenter (Mitsuwa Rikagaku Kogyo Co.; KMJ-5A), and fermented up to 3% acetic acid concentration. Then, the culture medium was withdrawn from the mini-jar fermenter with 700 ml of it left, 1.8 L of YPG medium containing 100 µg/ml of ampicillin was newly added, it was adjusted to the concentration of 4% ethanol and 1% acetic acid, and fermentation was thus restarted. The concentration of ethanol in the medium was maintained at 1% by addition of ethanol during the fermentation, and still further acetic acid fermentation was performed. Then, acetic acid fermentation ability of the transformant was compared to that of the original strain. The result was summarized in Table 1.

TABLE 1

| | Final acetic acid concentration (%) | Specific growth rate (OD660/hr) | Production rate (%/hr) | Growth lag-time (hr) |
| --- | --- | --- | --- | --- |
| Original strain | 9.5 | 0.0151 | 0.103 | 62.5 |
| Transformant | 11.1 | 0.0323 | 0.136 | 24.0 |

From the result of Table 1, it was confirmed that the transformant was apparently superior in any of final acetic acid concentration, specific growth rate, production rate, and growth lag-time.

Example 4

Enhancement of Acetic Acid Tolerance in the Transformant Transformed with Acetic Acid Resistance-Gene Derived from *Gluconacetobacter entanii*

(1) Transformation of *Acetobacter altoacetigenes*

Plasmid pSPT obtained in Example 2 was transformed into *Acetobacter altoacetigenes* MH-24 strain (FERMBP-491) which was one strain of *Gluconacetobacter entanii* by electroporation method (see non-patent literature 6, for instance). The transformant was selected on YPG agar medium containing 0.55% agar added 100 µg/ml of ampcillin, 4% acetic acid and 4% ethanol.

The ampicillin-resistant transformant grown on the selection medium was extracted plasmid in the conventional manner for analysis and it was confirmed that they retained the plasmid having SPT gene.

Specifically, they were cultured with agitation rate at 500 rpm, aeration rate at 0.20 vvm and temperature of 30° C. in 2.5 L of YPG medium containing 4% acetic acid, 4% ethanol, and 100 µg/ml of ampicillin using 5 L of mini-jar fermenter (Mitsuwa Rikagaku Kogyo Co.; KMJ-5A), and fermented up to 6.3% acetic acid concentration. Then, the culture medium was withdrawn from the mini-jar fermenter with 700 ml of it left, 1.8 L of YPG medium containing 100 µg/ml of ampicillin was newly added, it was adjusted to the concentration of 6% and 4% ethanol, and fermentation was thus restarted. The concentration of ethanol in the medium was maintained at 1% by addition of ethanol during the fermentation, and still further acetic acid fermentation was performed. Then acetic acid fermentation ability of the transformant was compared to that of the original strain. The result was summarized in Table 2.

TABLE 2

| | Final acetic acid concentration (%) | Specific growth rate (OD660/hr) | Production rate (%/hr) |
| --- | --- | --- | --- |
| Original strain | 14.6 | 0.501 | 0.142 |
| Transformant | 16.2 | 0.756 | 0.175 |

From the result of Table 2, it was confirmed that transformants were apparently superior in any of final acetic acid concentration, specific growth rate, production rate, and growth lag-time.

Example 5

Cloning of Acetic Acid Resistance-Gene from *Acetobacter aceti* and Determination of the Nucleotide Sequence and the Deduced Amino Acid Sequence

*Acetobactger aceti* No. 1023 strain (FERM BP-2287) was performed shaking culture on YPG medium (3% glucose, 0.5% yeast extract and 0.2% polypeptone) at 30° C. for 24 h. After the cultivation, culture medium was centrifuged (7,500×g, 10 min) and bacterial cells were obtained. Chromosomal DNA was prepared from obtained bacterial cells by chromosomal DNA preparation method (see patent literature 3, for instance).

Cloning was conducted by inverse PCR method using above-prepared DNA as a template. Specifically, primer 3 (the nucleotide sequence thereof is shown in SEQ. ID No. 7 (FIG. 9)) and primer 4 (the nucleotide sequence thereof is shown in SEQ. ID No. 8 (FIG. 10)) were synthesized from domains which were thought to have higher conservation in comparison with other species from DNA sequence (SEQ. ID No. 1) obtained in *Acetobacter altoacetigenes* MH-24 strain. Next, PCR reaction was carried out using chromosomal DNA of *Acetobacter aceti* No. 1023 strain as a template, and approximately 750 bp of amplified fragments were obtained. Then, chromosomal DNA of *Acetobacter aceti* No. 1023 strain was completely digested by restriction enzyme PstI, and legations were performed in the conventional manner. PCR was performed using primer 5 (the nucleotide sequence thereof is shown in SEQ. ID No. 9 (FIG. 11)) and primer 6 (the nucleotide sequence thereof is shown in SEQ. ID No. 10 (FIG. 12)) and using the ligation product as a template and approximately 3 kbp of amplified fragment was obtained.

As a result of sequencing the nucleotide sequences of this fragment by Sanger's dideoxy chain-termination method using above-mentioned primers, the nucleotide sequence shown in SEQ. ID No. 3 was determined. Sequencing was conducted in the all domains of the both of strands of DNA.

Example 6

Enhancement of Acetic Acid Tolerance in the Transformant Transformed with Acetic Acid Resistance-Gene Derived from *Acetobacter aceti*

(1) Transformation of *Acetobacter altoacetigenes*

Plasmid pSPT2 obtained in Example 5 were transformed into *Acetobacter* altoacetigenes MH-24 strain (FERM BP-491) which was one strain of *Gluconacetobacter entanii* by electroporation method (see non-patent literature 6, for instance). The transformants were selected on YPG agar media containing 0.55% agar added 100 µg/ml of ampcillin, 4% acetic acid and 4% ethanol.

The transformants having ampicillin tolerance, grown on the selection medium, were extracted plasmids in the conventional manner for analysis and it was confirmed that they retained the plasmids including SPT gene.

Specifically, they were cultured with agitation rate at 500 rpm, aeration rate at 0.20 vvm and temperature of 30° C. in 2.5 L of YPG medium containing 4% acetic acid, 4% ethanol, and 100 µg/ml of ampicillin using 5 L of mini-jar fermenter (Mitsuwa Rikagaku Kogyo Co.; KMJ-5A), and fermented up to 6.3% acetic acid concentration. Then, the culture medium was withdrawn from the mini jar fermenter with 700 ml of it left, 1.8 L of YPG medium containing 100 µg/ml of ampicillin was newly added, it was adjusted to the concentration of 6% and 4% ethanol, and fermentation was thus restarted. The concentration of ethanol in the medium was maintained at 1% by addition of ethanol during the fermentation, and still further acetic acid fermentation was performed. Then, acetic acid fermentation ability of the transformant was compared to that of the original strain. The result was summarized in Table 3.

TABLE 3

|  | Final acetic acid concentration (%) | Specific growth rate (OD660/hr) | Production rate (%/hr) |
| --- | --- | --- | --- |
| Original strain | 14.6 | 0.501 | 0.142 |
| Transformant | 16.0 | 0.605 | 0.153 |

From the result of Table 3, it was confirmed that the transformants were apparently superior in any of final acetic acid concentration, specific growth rate, production rate, and growth lag-time.

INDUSTRIAL APPLICABILITY

According to the present invention, novel genes participating in acetic acid tolerance can be provided, further bred strain capable of efficiently producing vinegar at higher acetic acid concentration by using the genes can be obtained. Still further, the present invention enables to furnish a method of efficiently producing vinegar at higher acetic acid concentration using the bred strain.

The invention claimed is:

1. An isolated DNA that is a DNA described in the following (a), (b) or (c):
   (a) a DNA that comprises the nucleotide sequence of nucleotides 187 to 1386 shown in SEQ ID NO:1;
   (b) a DNA that completely hybridizes with a probe comprising the complement of the entire length of the nucleotide sequence consisting of nucleotides 187 to 1386 shown in SEQ ID NO:1 under a stringent condition, wherein said DNA encodes a protein having a function of enhancing acetic acid tolerance: or
   (c) a DNA that encodes a protein comprising the amino acid sequence of SEQ ID NO:2.

2. A recombinant plasmid pUSPT (FERM BP-7932) comprising the nucleotide sequence of SEQ ID NO:1.

* * * * *